US010308716B2

(12) United States Patent
Stech et al.

(10) Patent No.: US 10,308,716 B2
(45) Date of Patent: Jun. 4, 2019

(54) METHOD FOR PRODUCING POLYCLONAL ANTIBODIES USING AN ANTIGENIC COMPOSITION COMPRISING PROTEIN-CONTAINING MEMBRANE VESICLES

(71) Applicant: Fraunhofer-Gesellschaft zur Foerderung der angewandten Forschung e. V., Munich (DE)

(72) Inventors: Marlitt Stech, Potsdam (DE); Katja Hanack, Berlin (DE); Katrin Messerschmidt, Potsdam (DE); Stefan Kubick, Berlin (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 307 days.

(21) Appl. No.: 15/027,775

(22) PCT Filed: Sep. 24, 2014

(86) PCT No.: PCT/EP2014/002592
§ 371 (c)(1),
(2) Date: Apr. 7, 2016

(87) PCT Pub. No.: WO2015/055277
PCT Pub. Date: Apr. 23, 2015

(65) Prior Publication Data
US 2016/0251439 A1 Sep. 1, 2016

(30) Foreign Application Priority Data
Oct. 15, 2013 (EP) .................................. 13004943

(51) Int. Cl.
*C07K 16/18* (2006.01)
*A61K 39/395* (2006.01)
*C07K 16/28* (2006.01)
*C07K 14/435* (2006.01)
*A61K 39/39* (2006.01)
*C07K 16/30* (2006.01)
*A61K 39/00* (2006.01)

(52) U.S. Cl.
CPC .......... *C07K 16/2863* (2013.01); *A61K 39/39* (2013.01); *C07K 14/43563* (2013.01); *C07K 16/18* (2013.01); *C07K 16/30* (2013.01); *A61K 2039/505* (2013.01); *A61K 2039/54* (2013.01); *A61K 2039/572* (2013.01); *A61K 2039/585* (2013.01); *C07K 2317/10* (2013.01); *C12N 2710/24133* (2013.01)

(58) Field of Classification Search
None
See application file for complete search history.

(56) References Cited

U.S. PATENT DOCUMENTS

2004/0191858 A1* 9/2004 Ezure ..................... C12N 1/066
435/68.1
2006/0233789 A1* 10/2006 Endo ................... C07K 14/445
424/133.1

FOREIGN PATENT DOCUMENTS

WO 0028001 A1 5/2000
WO 03016522 A2 2/2003

OTHER PUBLICATIONS

Nishimura et al. Langmuir, 2012, vol. 28, p. 8426-8432.*
Haurum, "Recombinant polyclonal antibodies: the next generation of antibody therapeutics?", Drug Discovery Today, 11(13-14), 655-660 (2006).
Katzen et al., "The past, present and future of cell-free protein synthesis", Trends Biotechnol., 23(3), 150-156 (2005).
Shaklee et al., "Protein Incorporation in Giant Lipid Vesicles under Physiological Conditions", CHEMBIOCHEM., 11(2),175-179 (2010).
Stech et al., "Cell-free systems: functional modules for synthetic and chemical biology", Advanced Biochemical Engineering Biotechnology, 137, 67-102 (2013).
International Search Report of PCT/EP2014/002592 dated Jun. 3, 2015.
Amidi et al. (2011). Antigen-expressing immunostimulatory liposomes as a genetically programmable synthetic vaccine. Systems and Synthetic Biology, 5, 21-31.
Goren et al. (2009). Cell-free translation of integral membrane proteins into unilamelar liposomes. Methods in Enzymology, 463, 647-673.
JPO, Jun. 25, 2018 Office Action in JP 2016-523216 (Translation).
Stech et al. (2012). Production of functional antibody fragments in a vesicle-based eukaryotic cell-free translation system. Journal of Biotechnology, 164, 220-231.
Suzuki et al. (2009). Preparation of ubiquitin-conjugated proteins using an insect cell-free protein synthesis system. Journal of Biotechnology, 145, 73-78.

(Continued)

*Primary Examiner* — Yunsoo Kim
(74) *Attorney, Agent, or Firm* — Caesar Rivise, PC

(57) ABSTRACT

The invention relates to a method for producing polyclonal antibodies against an antigenic target protein which comprises inducing an immune response in a host by applying an immunogenic composition comprising membrane vesicles incorporating said antigenic target protein to said host and obtaining antibodies against said target protein from the host's serum. A more specific embodiment of this method comprises at least the following steps: a) synthesizing the target protein my means of an in vitro translation reaction in a reaction medium comprising a nucleic acid template coding for the target protein and a cell lysate which contains membrane vesicles; b) separating membrane vesicles comprising the synthesized target protein from the medium; c) providing the membrane vesicles comprising the synthesized target protein in a physiologically compatible medium; d) applying the membrane vesicles of step c) to a host; e) testing a serum sample of the host for a specific immune response against said target protein; and f) obtaining specific antibodies against said target protein from the serum of a host exhibiting a specific immune response against said target protein.

14 Claims, 5 Drawing Sheets

(56) References Cited

OTHER PUBLICATIONS

Shaklee et al. (2010). Protein incorporation in giant lipid vesicles under physiological conditions. ChemBioChem 11, 175-179.
Chinese Office Action dated Dec. 24, 2018 for Chinese Patent Application No. 201480055072.4.

* cited by examiner

METHOD FOR PRODUCING POLYCLONAL ANTIBODIES USING AN ANTIGENIC COMPOSITION COMPRISING PROTEIN-CONTAINING MEMBRANE VESICLES

BACKGROUND OF THE INVENTION

Antibodies are powerful and invaluable tools in diagnostics and therapeutics. In accordance with the growing demand of highly specific antibodies, a number of different strategies have been developed over time in order to allow a reliable production of antibodies in sufficient amounts (see, e.g., J. S. Haurum, *Drug Discovery Today*, 2006. 11(13-14), 655-660). In this context, the discovery of the hybridoma technology in 1975 represents a significant breakthrough as mouse hybridomas were the first reliable source of monoclonal antibodies.

In theory, monoclonal antibodies can be developed against any target of choice. The provision of the target of choice is absolute essential. Even in the case of genetic immunization the antigen is required for screening and confirmation purposes. Unfortunately, in some cases provision of the antigen might become a problem if neither antigen isolation nor production in cell-based assays is successful.

Usually, the antigen belongs to the class of proteins and peptides, but principally also other substance classes can be used as immunogen as for example polysaccharides, lipids and polynucleotides. In most cases, antibodies shall be generated against the native antigen. If the antigen is produced by recombinant DNA technology, it is very important to compare the properties of the resulting recombinant protein or peptide with its native counterpart since differences in the protein structure may lead to differences in the immunogenicity. Proteins and peptides are highly interesting targets for antibody production. Peptide synthesis represents an alternative for cell-based expression given the fact that the immunogenic epitope is linear and not dependent on the tertiary structure of the intact protein. On the other hand, peptide synthesis has its limitations for proteins and peptides with posttranslational modifications (PTMs) which are part of the three-dimensional epitope. Furthermore, usage of peptides and peptide mixtures as antigen may induce the generation of cross-reactive antibodies.

Membrane proteins account for nearly one third of all sequenced genomes. In contrast to their crucial involvement in cellular processes such as signaling, metabolism, transport and recognition, little information is available about membrane protein structures and functionality. The deregulation of their biological activity in vivo can lead to severe diseases, making them highly interesting pharmacological targets. This development caused an increase in the demand of membrane protein specific antibodies.

The generation of specific antibodies against membrane proteins is often limited by the inability to produce or isolate a certain target membrane protein. Overexpression of membrane proteins in vivo is often hampered by protein misfolding, insolubility, aggregation, low productions yields and cell cytotoxicity. However, cell-free expression of membrane proteins can overcome these obstacles.

Over the last decade, cell-free protein synthesis has become a valuable tool for the production of different protein classes including membrane proteins, cytosolic or even toxic proteins (see, e.g. Katzen et al., *Trends Biotechnol.*, 2005. 23(3), 150-156). The basis of an efficient cell-free expression system is a translationally active cell extract which contains the essential components for translation such as ribosomes, translation factors and enzymes. Furthermore, the cell lysate is supplemented with amino acids, ATP and GTP and an energy regenerating system (e.g. creatine-phosphate/creatine-kinase energy-regenerating system). Synthesis of the target protein is initiated by addition of an appropriate template either in form of DNA or mRNA. Until now, many different types of functionally active target proteins have been expressed in prokaryotic and eukaryotic cell-free systems. In comparison to prokaryotic cell extracts eukaryotic cell lysates offer several advantages in the expression of complex proteins which require posttranslational modifications.

Nevertheless, the use of the proteins synthesized by means of prokaryotic and eukaryotic cell lysates for the production of specific antibodies according to the conventional methods of the prior art still involves additional laborious purification and/or isolation steps in order to provide the desired target protein in a suitable form for use as an immunogenic substance.

In view of the drawbacks of the prior art, the main object of the present invention was to provide improved methods and means for producing polyclonal antibodies against a specific target protein.

This objective has been achieved by providing the novel methods for producing polyclonal antibodies against a specific target protein using an antigenic composition comprising protein-containing membrane vesicles according to the invention.

DESCRIPTION OF THE INVENTION

The method for producing polyclonal antibodies against an antigenic target protein according to claim 1 comprises inducing an immune response in a host by applying an immunogenic composition comprising membrane vesicles incorporating said antigenic target protein to said host and obtaining antibodies against said target protein from the host's serum.

The more specific method according to claim 2 comprises at least the following steps:

a) synthesizing the target protein my means of an in vitro translation reaction in a reaction medium comprising a nucleic acid template coding for the target protein and a cell lysate which contains membrane vesicles;
b) separating membrane vesicles comprising the synthesized target protein from the medium;
c) providing the membrane vesicles comprising the synthesized target protein in a physiologically compatible medium;
d) applying the membrane vesicles of step c) to a host;
e) testing a serum sample of the host for a specific immune response against said target protein; and
f) obtaining specific antibodies against said target protein from the serum of a host exhibiting a specific immune response against said target protein.

Investigations of the present inventors surprisingly demonstrated that it is possible to use a preparation of membrane vesicles having incorporated at least one target protein, directly as an immunogenic composition for raising specific antibodies against the target protein(s) in a host. Such a membrane vesicle preparation is essentially non-toxic for the host and can be advantageously used to induce a strong immune response without adding any further immunostimulatory agents.

A suitable membrane vesicle preparation is, e.g., obtained after performing a cell-free translation reaction in a reaction medium comprising a nucleic acid template coding for a target protein and a cell lysate which contains membrane vesicles, and separating the protein-containing vesicles after the translation reaction from the medium.

Preferably, the cell lysate is a eukaryotic cell lysate.

Said eukaryotic cell lysate is not especially limited and may be principally any cell lysate which contains all the components required for the in vitro translation of the nucleic template used and, optionally, modification of the target protein synthesized.

More specifically, the eukaryotic cell lysate is selected from the group comprising wheat germ lysates, insect cell lysates, in particular Sf21 cell lysates, reticulocyte lysates, keratinocyte lysates, cell extracts from CHO cells, HeLa cells, myeloma cells, hybridoma cells or cultivated lymphoma cells.

These cell lysates may be used in their native form or modified by adding or removing specific components.

The cell-free system used in the examples below is based on translationally active lysates generated from cultured insect cells (*Spodoptera frugiperda*, Sf21). By a very gentle lysate preparation procedure which retains the integrity of subcellular components, vital parts of the endoplasmic reticulum (ER) can be maintained in the lysate as functionally active membranous vesicles. Using a vesicle-containing type of lysate, post-translational modifications (PTMs) such as glycosylation, signal peptide cleavage, lipidation, phosphorylation and disulfide bond formation can be performed on target proteins.

If the primary cell lysate obtained from a specific cell line does not contain membrane vesicles (such as reticulocyte lysates), vesicles may be added from a different source, e.g. from the lysate of a different cell line.

Preferably, the membrane vesicles and the cell lysate are derived from the same cell line.

Further, artificial cell lysates wherein one or more components have been prepared synthetically may be used as well.

The reaction medium for the in vitro translation reaction comprises said cell lysate which contains the essential components for translation such as ribosomes, translation factors and enzymes. Furthermore, the medium or cell lysate is supplemented with amino acids, ATP and GTP and an energy regenerating system (e.g. creatine-phosphate/creatine-kinase energy-regenerating system). Synthesis of the target protein is initiated by the addition of an appropriate nucleic acid template for the target protein, either in form of DNA or mRNA.

The membrane vesicles comprising the synthesized target protein may be separated from a reaction medium by any suitable method known in the art, in particular by means of centrifugation or filtration.

In a preferred embodiment of the invention, the in vitro translation reaction in step a) is effected under conditions which promote the enrichment of the synthesized target protein in the membrane vesicles.

One exemplary approach for obtaining such an enrichment of the synthesized target protein in membrane vesicles involves a modification of the method according to claim 2, wherein step b) of claim 2 is followed by an additional step b') which comprises transferring the separated membrane vesicles into a secondary reaction medium comprising a nucleic acid template coding for the target protein and a cell lysate which does not contain membrane vesicles, performing an in vitro translation reaction in said secondary reaction medium, and separating membrane vesicles comprising an increased amount of the synthesized target protein from the secondary medium, wherein step b' may be repeated one or more times.

In an alternative embodiment, the in vitro translation reaction in step a) is performed by means of a continuous dialysis-based method involving the addition and/or discharge of reactants or products in the course of the translation reaction. This reaction format prolongs the reaction life time and thus increases the overall protein yield.

Typically, this embodiment is realized in a device which comprises at least 2 compartments separated by means of a dialysis membrane, wherein the translation reaction takes place in at least one first compartment, the reaction compartment, and in the course of the translation reaction reactants from at least one further compartment, the charge and discharge compartment, diffuse into the reaction compartment, and reaction by-products diffuse from the reaction compartment into the charge and discharge compartment.

Preferably, a caspase inhibitor is present in at least the reaction compartment. As shown in the co-pending patent application DE 10 2013 015 977.6, filed on 25 Sep. 2013, the presence of a caspase inhibitor during the in vitro translation reaction considerably increases the protein yield in a cell-free translation system wherein an eukaryotic cell lysate is used.

In a typical embodiment of the claimed method, the immunogenic composition with the protein-containing membrane vesicles applied to the host does not contain any additional immunostimulatory adjuvant. As already mentioned, the immunogenic composition used in the present invention advantageously allows to dispense with further auxiliary agents.

In said immunogenic composition, the vesicles may be provided in any suitable physiologically compatible medium or buffer known in the art. In particular, the pH and salt concentration of a "physiologically compatible" medium or buffer has to be physiologically compatible with the body of the intended host. The physiologically compatible medium may be for example PBS but suitable alternatives will be readily recognized by a person skilled in the art.

The host used for immunization and obtaining the specific polyclonal antibodies, may be any host animal used for such purposes in the art. Typically, it is a non-human mammal, such as a rodent, including a mouse or rat, goat, sheep, cattle etc.

A closely related aspect of the invention relates to a method for accumulating a target protein in the vesicles of a membrane vesicle preparation, comprising at least the following steps:

a) synthesizing the target protein my means of an in vitro translation reaction in a reaction medium comprising a nucleic acid template coding for the target protein and a cell lysate which contains membrane vesicles;

b) separating membrane vesicles comprising the synthesized target protein from the medium;

c) transferring the separated membrane vesicles into a secondary reaction medium comprising a nucleic acid template coding for the target protein and a cell lysate which does not contain membrane vesicles, performing an in vitro translation reaction in said secondary reaction medium, and separating membrane vesicles comprising an increased amount of the synthesized target protein from the secondary medium, wherein step c) may be repeated one or more times.

The present application discloses a novel methodology which enables the generation of polyclonal antibodies against difficult-to-express proteinogenic antigens, for example membrane proteins and proteins with post-translational modifications, in a fast and efficient manner. The basis of this methodology is the use of a eukaryotic cell-free translation system for the synthesis, translocation and embedding of the target protein into ER-derived membranous vesicles which are present in the lysate. Following cell-free protein synthesis, the vesicles with their embedded target protein can be separated from the cytosolic fraction of the lysate and can subsequently be used as cargo vehicles for the processing of the embedded antigen.

The entire methodology may be described in 5 principal steps as indicated in FIG. 1 for a target membrane protein.

1. Cell-free synthesis of the target protein. Cell-free synthesis of the target protein should be performed in a translation system that enables the synthesis of a given target protein in a soluble and correctly folded state. In the case of membrane proteins the presence of a synthetic or natural lipid or detergent scaffold is required. The cotranslational translocation of the target protein into the lumen of the vesicles or the embedding of a de novo synthesized target membrane protein into the lipid double layer is initiated by one ore more signal sequences in the respective protein sequence.

This first step may also include a cumulative enrichment of target (membrane) proteins in the membrane or lumen of ER-derived vesicles. In order to enrich the fraction of de novo synthesized proteins in comparison to the fraction of endogenous proteins, a repetitive synthesis can be performed. Here, the target protein is synthesized in several subsequently performed cell-free reactions into the same batch of insect vesicles. After each synthesis step, the vesicles are harvested and applied to the next synthesis step resulting in a continuous increase of the exogenous membrane protein present in the vesicle membrane. Thus it is possible, to increase the protein yield from typically 1 to 10 µg/ml as obtained in a standard batch reaction to about 20 to 30 µg/ml.

2. Harvest of ER-derived vesicles, containing de novo synthesized (membrane) proteins, preferably by centrifugation. ER-derived vesicles can be separated from the cytosolic part of the lysate by a single centrifugation step. After centrifugation vesicles are resuspended in a medium or buffer having a physiological pH and salt concentration, such as phosphate-buffered saline (PBS), and washed in this medium/buffer in order to remove cytosolic proteins which may be attached to the vesicles.

3. Harvested and washed vesicles with their incorporated target protein can be used as immunogen. The vesicle-buffer solution is injected directly into laboratory animals.

4. Blood taking, preferably after a suitable period of rest, e.g. 4 weeks.

5. Performance of polyclonal mouse antiserum with respect to antigen recognition is evaluated, e.g. by a western blot.

In the case of positive results, the corresponding blood donor can be considered as a source for the production of monoclonal antibodies.

REFERENCE EXAMPLE

Figure 1:
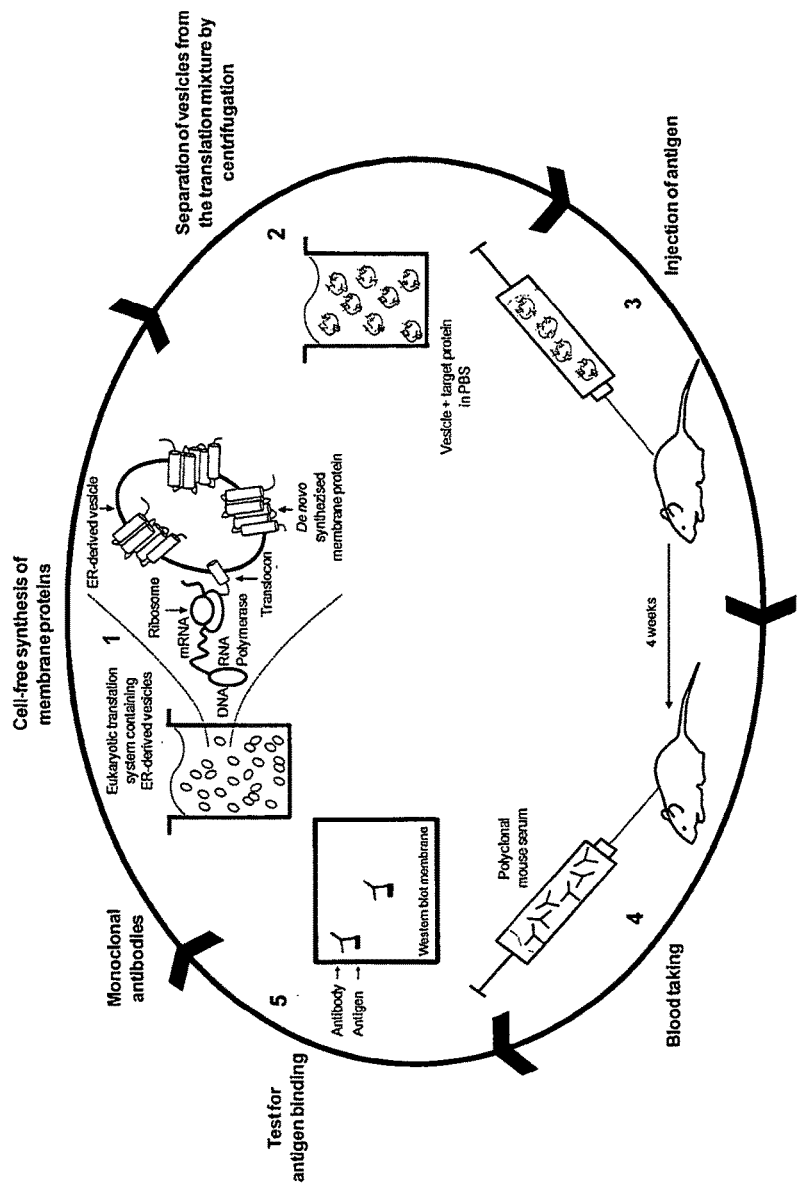
FIG. 1 Schematical overview of the generation of specific antibodies through immunization of mice with cell-free synthesized membrane proteins by using an eukaryotic, vesicle-based translation system FIG. 2 Western blot analysis of mouse polyclonal antiserum gained before and after immunization of mice with insect vesicles FIG. 3 Analysis of cell-free synthesized Mel-trunc-EGFR by TCA-precipitation and subsequent liquid scintillation counting and autoradiography FIG. 4 His-Tag purification of cell-free synthesized Mel-trunc-EGFR-His using an insect lysate
A) Coomassie stain of the SDS-PAGE gel after gel electrophoresis
B) Detection of Mel-trunc-EGFR-His by western blot using a commercially available anti-EGF receptor antibody (Anti-EGF receptor D38B1 XP) as primary antibody and a HRP-coupled anti-rabbit antibody as secondary antibody (HRP-conjugated Anti-rabbit IgG)

Immunization of Murine Hosts with Membrane Vesicles Harboring Endogenous Proteins and Analysis of the Antisera The eukaryotic translation system used in these experiments is based on translationally active lysates derived from cultured *Spodoptera frugiperda* (Sf21) cells and contains functionally endogenous membranous vesicles which have their origin in the endoplasmatic reticulum (ER) of Sf21 insect cells.

In a first step, it was investigated whether injection of insect vesicles and their incorporated endogenous proteins into mice can cause an immune reaction. Secondly, it was investigated whether insect vesicles can cause an immune reaction even without addition of Freund's adjuvant.

For this purpose eight laboratory mice were injected with different mixtures of insect vesicles, Freund's adjuvant and PBS (Table 1). Seven out of eight animals survived until the final blood taking. Blood taking from all animals was performed immediately before the first immunization and one week after the second and final immunization.

TABLE 1

Overview of the applied immunogens. Every lab mouse was immunized with a total volume of 120 µl antigen solution.

|   | Volume PBS [µl] | Volume vesicle solution [µl] | Volume Freund's adjuvant [µl] | Number of immunized mice |
|---|---|---|---|---|
| 1 | 120 | — | — | 2 |
| 2 | 60 | 60 | — | 2 |
| 3 | — | 60 | 60 | 2 |
| 4 | 60 | — | 60 | 2 |

Before immunization membranous vesicles were prepared in the following way: Insect vesicles were separated from the soluble fraction of the lysate by a centrifugation step at 16.000 g (10 min, 4° C.). The supernatant (SN) was discarded and the resulting vesicular fraction (VF) was washed three times in the double volume of PBS buffer. After the third washing step VF was resuspended in the original volume of insect lysate. An aliquot of this solution was diluted 1:2 in PBS buffer. 120 µl of this solution was used for intraperitoneal immunization of two laboratory mice (strain BALB/c). Six additional laboratory animals were injected with the following solutions: Two animals with 120 µl PBS, two animals with insect vesicles resuspended in PBS and mixed with Freund's adjuvant (ration 1:1) and two animals with a mixture of PBS buffer and Freund's adjuvant (ratio 1:1). After two weeks of rest, a second immunization ("boost") was performed in analogy to the first one. One week after the second immunization, blood was taken from all animals which had survived. Obtained antiserum was stored at −20° C. until further usage.

Analysis of the Antiserum

Obtained polyclonal mouse antisera were analyzed by western blot. Usually, polyclonal antisera are analyzed by ELISA, a test method in which the antigen that has been used for immunization is coated onto the microtiter plate. Here, another strategy is employed as the antigen represents a lipid-protein-mixture which hardly can be immobilized by using standard procedures. Thus, interactions between antibodies and antigens were analyzed by western blot.

For this purpose the antigens used for immunization were prepared in the following manner: Insect vesicles were separated from the cytosolic fraction of the lysate by centrifugation as described above and washed three times in PBS. Afterwards, aliquots of SN and VF were precipitated in acetone and separated in a 10% SDS-PAGE (NuPAGE®, 10% Bis-Tris gels MES SDS buffer, Life technologies).

Proteins were transferred onto polyvinylidine fluoride (PVDF) membranes (life technologies) using the semi-dry-blot technique (semi-dry blotting; iBlot system, life technologies, program 3). After blotting, membranes were covered with 25 ml of TBS buffer for 5 min at room temperature, followed by incubation in 25 ml blocking solution (1× Roti Block, Roth) for 1 h at room temperature or over night at 4° C. After blocking, membranes were washed three times with 15 ml TBS/Tween. Then, membranes were sliced into parts containing the lysate fractions SN and VF.

Membrane slices were incubated for 1 h at room temperature with the different polyclonal mouse antisera, diluted 1:2000 in blocking buffer. After three times washing with TBS/Tween membrane slices were incubated with horseradish peroxidase (HRP)-coupled anti-mouse antibody (anti-mouse conjugated IgG, 1:1000 in blocking buffer). After three times washing in TBS/Tween secondary antibodies were detected by incubation of membrane slices with a chemiluminescent detection reagent (ECL plus western blotting detection reagent, GE Healthcare) which was incubated for 5 min. Emitted light was detected using the phosphorimager system (Typhoon TRIO+Imager, GE Healthcare) (emission maximum 425 nm).

Figure 2:
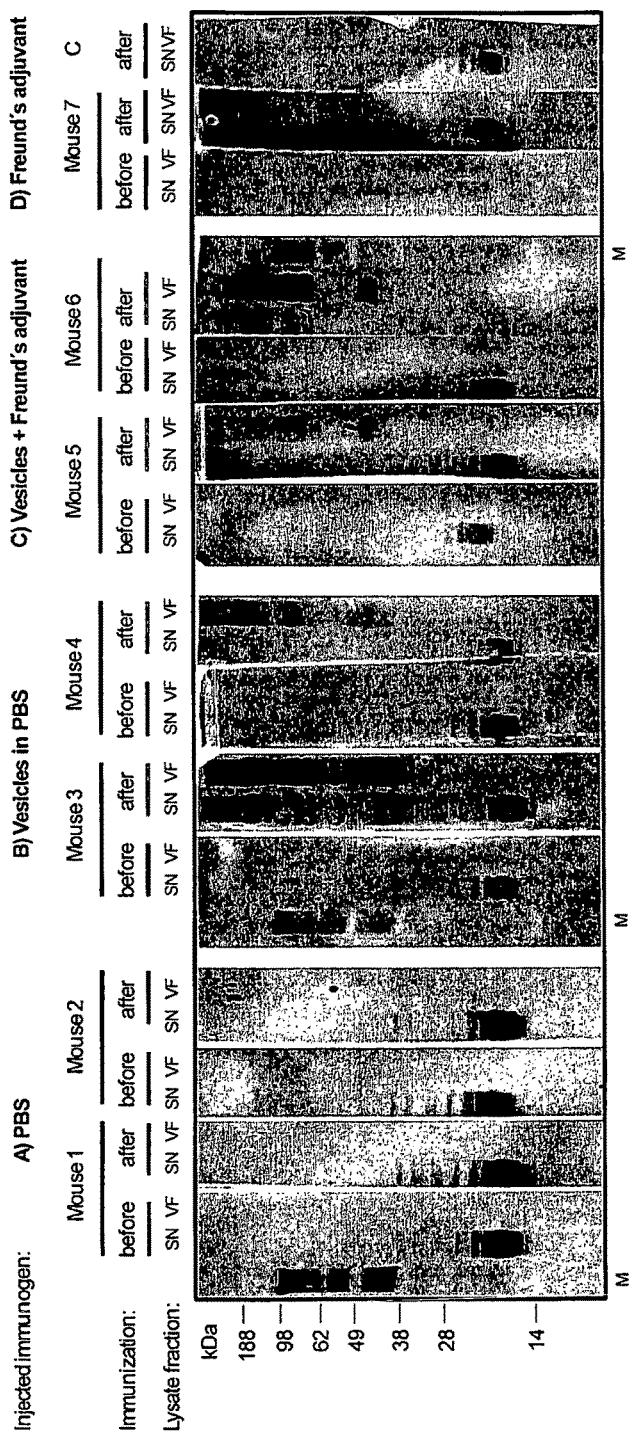

The resulting western blot is presented in FIG. 2: western blot analysis of mouse polyclonal antiserum gained before and after immunization of mice with insect vesicles. Immunization of animals was performed with 120 µl PBS (A), 120 µl vesicles in PBS (B), 120 µl vesicles in PBS supplemented with Freund's adjuvant as well as 120 µl Freund's adjuvant. Immunogen A represents the control for B) and C); immunogen D represents the control for C). Membrane slices were incubated for 1 h at room temperature with the polyclonal mouse serum (dilution 1:2000 in blocking buffer), followed by incubation with HRP-coupled anti-mouse antibody (anti-mouse conjugated IgG, dilution 1:1000 in blocking buffer). M=protein marker (SeeBlue® Plus2, Life technologies). C=Specificity control for secondary HRP-coupled anti-mouse antibody. This membrane slice was treated as the others, with the only exception that it was not incubated with polyclonal mouse serum.

Appliance of a mouse antiserum that was gained before immunization did not enable a specific detection of insect proteins in the two analyzed lysate fractions SN and VF. Solely, a non-specific reaction of the secondary antibody with proteins from SN was observed (FIG. 2, lane C, membrane slice was not incubated with mouse serum, but only with the secondary antibody).

Incubation of SN and VF membrane slices with mouse serum gained after immunization led to detection of a broad range of different proteins in VF, but not in SN. In this context it was observed that supplementation of insect vesicles with Freund's adjuvant did not have a positive effect on the intensity of the immune reaction.

The results presented in FIG. 2 demonstrate that insect vesicles with their embedded endogenous proteins were capable of inducing a sufficient immune reaction in mice. As controls two mice were immunized with PBS and Freund's adjuvant alone. As expected, sera obtained from these mice did not enable a detection of proteins.

EXAMPLE

Immunization of Murine Hosts with Membrane Vesicles Harboring Heterogenous Target Proteins and Analysis of the Antisera Cell-free Synthesis of Membrane Proteins in Insect Lysates A main object of this invention was to develop a new method which enables the production of antibodies against difficult-to-express membrane proteins in a fast and efficient manner.

As a model protein a truncated variant (vIII-Deletion) of the human epidermal growth factor receptor (EGFR) was chosen. This membrane protein, hereafter called Mel-trunc-EGFR, represents an interesting test candidate, since it is a permanently active mutant of full length EGFR, a protein which is involved in the development of certain cancer subtypes.

In order to increase the fraction of the target protein in the membrane of insect vesicles, five repetitive protein syntheses were preformed into the same set of vesicles. Cell-free protein synthesis in presence of $^{14}C$-leucine was performed as described in the following: The experiment was started with a batch-formatted translation reaction (1.5 h, 600 rpm) which was followed by centrifugation (16,000 g, 10 min, 4° C.) of the translation mixture (TM) and separation into SN and VF. SN was discarded while VF was resuspended in fresh, translationally active lysate without vesicles but supplemented with target nucleic acid (here mRNA). This procedure was repeated up to four times resulting in altogether five successive protein syntheses. In this way, the target protein Mel-trunc-EGFR was translocated into the same set of vesicles throughout the entire procedure.

Aliquots of 5 µl were taken from TM, SN and VF of the first and the last synthesis step and analyzed regarding protein yield, protein size and homogeneity.

Figure 3:
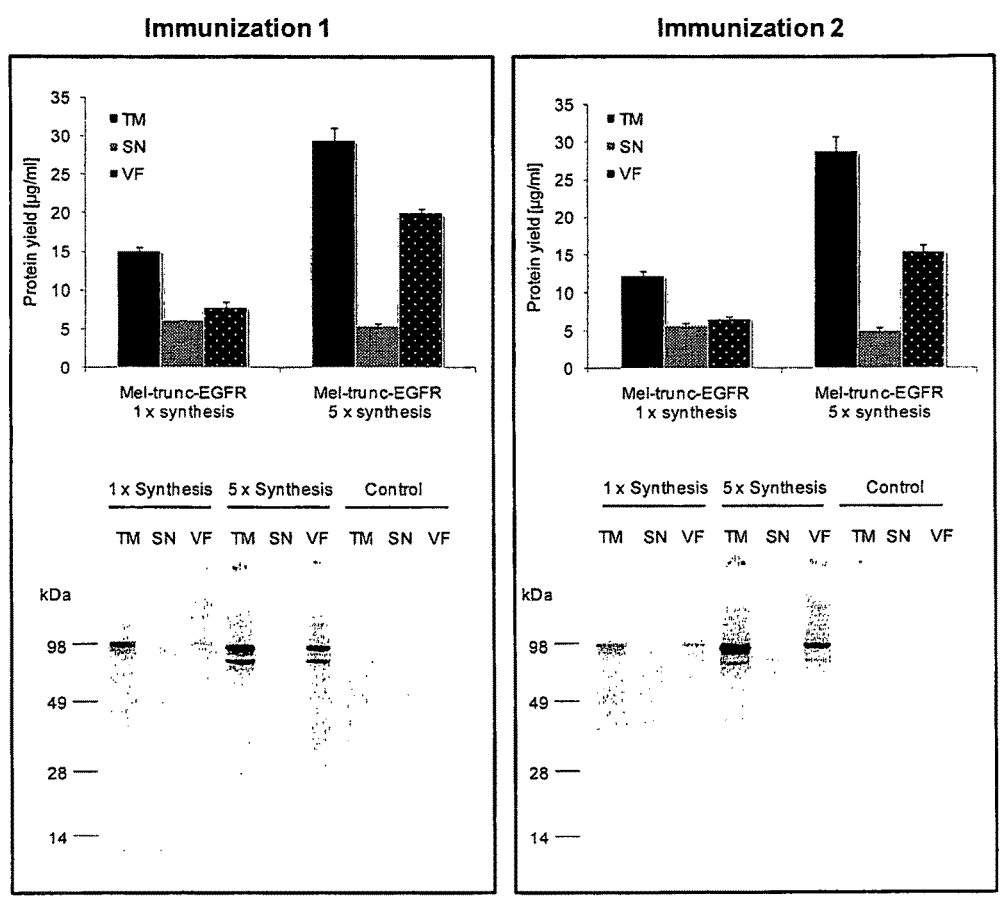

FIG. 3: Analysis of cell-free synthesized Mel-trunc-EGFR by TCA-precipitation and subsequent liquid scintillation counting and autoradiography. Cell-free protein synthesis was performed in presence of $^{14}C$-leucine using a eukaryotic translation system based on insect lysate. Analysis of Mel-trunc-EGFR in the translation mixture (TM), the supernatant fraction (SN) after centrifugation and the vesicular fraction (VF) was performed after a single synthesis (1× synthesis) and after five repeated syntheses (5× synthesis). Mel-trunc-EGFR shows an apparent molecular weight of approximately 98 kDa (calculated molecular weight 105 kDa).

Non-radioactive samples of Mel-trunc-EGFR were prepared in parallel and were applied for immunization.

The results presented in FIG. 3 show that after five repetitive syntheses the protein yield of Mel-trunc-EGFR in VF was increased from 7.8 µg/ml to 20.1 µg/ml (immunization 1) and 6.7 µg/ml to 15.6 µg/ml (immunization 2), resulting in a 2.5-fold increase of Mel-trunc-EGFR in VF from synthesis one to five. In parallel to the synthesis in presence of $^{14}$C-leucine non-radioactive samples of Mel-trunc-EGFR were prepared. Insect vesicles were harvested after five repeated syntheses and treated as described above. The insect vesicles with their contained exogenous target protein were used for immunization of two laboratory mice. The immunization procedure was performed as described before.

Purification of Mel-trunc-EGFR-His from Insect Vesicles

In order to demonstrate the presence of EGFR-specific antibodies in the polyclonal mouse antisera obtained, an analysis by western blot was performed.

For that purpose, the antigen (cell-free synthesized Mel-trunc-EGFR) was separated by SDS-PAGE and subsequently blotted onto a PVDF membrane. Cell-free synthesis of the antigen Mel-trunc-EGFR was performed in one synthesis step for 1.5 h, 500 rpm and 27° C. Afterwards, insect vesicles were harvested and washed three times in PBS as described above.

In addition, Mel-trunc-EGFR was purified from the vesicles via His-Tag purification. For this, a DNA-template of Mel-trunc-EGFR was used exhibiting a C-terminally fused His-tag. Purification of Mel-trunc-EGFR bearing the C-terminal His-Tag (Mel-trunc-EGFR-His) was performed as described in the following: Cell-free synthesis of Mel-trunc-EGFR-His was performed in one synthesis step in the same way as Mel-trunc-EGFR. After the synthesis, the translation mixture was separated into the lysate fractions SN and VF.

In order to release the membrane protein from the insect vesicles, VF was resuspended in PBS containing 1% of the mild detergent dodecyl-β-D-maltoside (DDM) and incubated over night at 4° C. Then, the solution was centrifuged (20.000 g, 1 h, 4° C.) and the resulting supernatant which contained the solubilized membrane protein was applied onto a Nickel-NTA matrix. Purification of Mel-trunc-EGFR-His was performed using the Qiagen® Ni-NTA Membrane Protein Kit according to the manufacturer's instructions. Samples of all different fractions were analyzed by SDS-PAGE and western blot using a commercially available anti-EGFR antibody as primary antibody (Anti-EGF receptor D38B1 XP, rabbit monoclonal antibody, 1:1000 in blocking buffer) and HRP-coupled antibody as secondary antibody (HRP-conjugated Anti-rabbit IgG, 1:2000 in blocking buffer). Detection of antigens was performed using a chemiluminescent detection reagent (ECL plus western blotting detection reagent, GE Healthcare).

Figure 4:
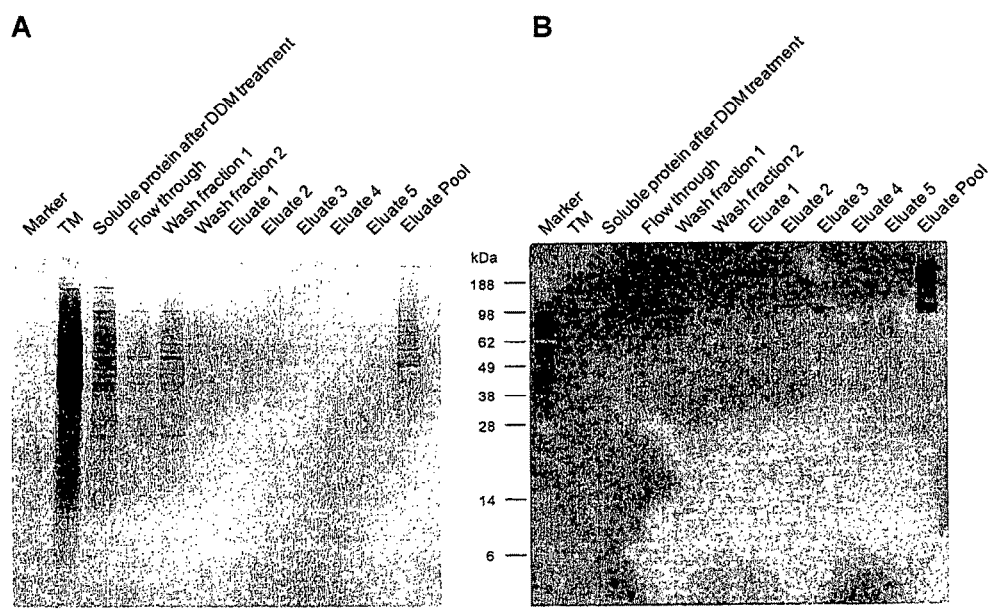

FIG. 4: His-Tag purification of Mel-trunc-EGFR-His. Cell-free synthesis of Mel-trunc-EGFR-His was performed using a eukaryotic translation system based on insect lysate.
A) Coomassie stain of the SDS-PAGE gel after gel electrophoresis.
B) Detection of Mel-trunc-EGFR-His by Western blot using a commercially available Anti-EGF receptor antibody (Anti-EGF receptor D38B1 XP, rabbit monoclonal antibody, 1:1000 in blocking buffer) as primary antibody and a HRP-coupled anti-rabbit antibody as secondary antibody (HRP-conjugated Anti-rabbit IgG, 1:2000 in blocking buffer). Mel-trunc-EGFR-His shows an apparent molecular weight of approximately 98 kDa (calculated molecular weight 105 kDa). Marker=protein marker SeeBlue® Plus2, Life technologies.

The Coomassie stain of the SDS-PAGE gel presented in FIG. 4 Fig. indicates the successful depletion of endogenous lysate proteins in eluate fractions one to five compared to the native translation mixture (TM). The target protein Mel-trunc-EGFR-His was detected in all tested fractions, except for washing fraction two and eluate one and two.

Analysis of Polyclonal Mouse Serum after Immunization with Mel-trunc-EGFR

In the next step, polyclonal mouse serum gained after immunization of mice with insect vesicles containing de novo synthesized Mel-trunc-EGFR was tested for detection of Mel-trunc-EGFR in a western blot. For that purpose, three different antigens were prepared: (i) Untreated insect vesicles, (ii) insect vesicles containing cell-free synthesized Mel-trunc-EGFR and (iii) purified Mel-trunc-EGFR-His. The antigens were separated by SDS-PAGE and blotted onto PVDF membranes. Western blot membrane slices were incubated with three different types of mouse sera: (a) Mouse serum gained before immunization (negative control), (b) mouse serum gained after immunization with insect vesicles alone without exogenous membrane protein and (c) serum gained after immunization with insect vesicles containing cell-free synthesized and membrane embedded Mel-trunc-EGFR.

Figure 5:
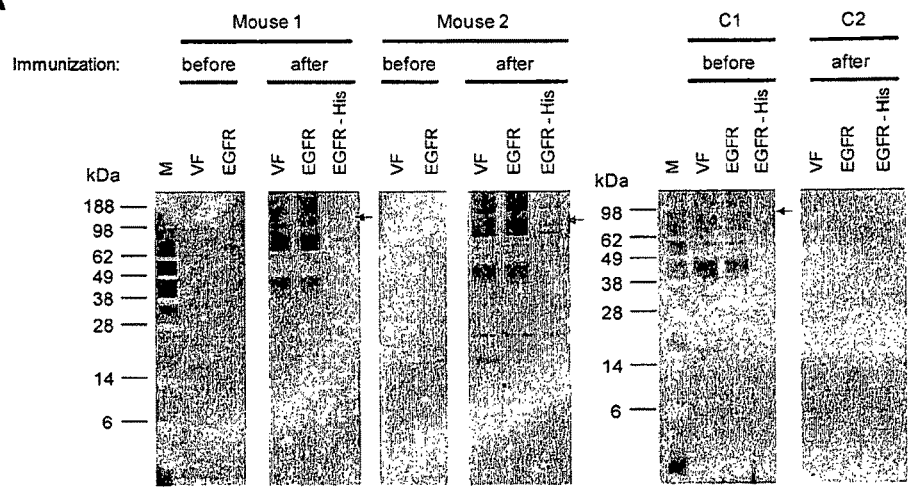
FIG. 5 Western blot analysis of mouse polyclonal antisera gained before and after immunization of mice with insect vesicles containing de novo synthesized Mel-trunc-EGFR The following non-limiting examples are provided to illustrate the present invention in more detail, however, without limiting the same to the specific features and parameters thereof.
Figure 5:
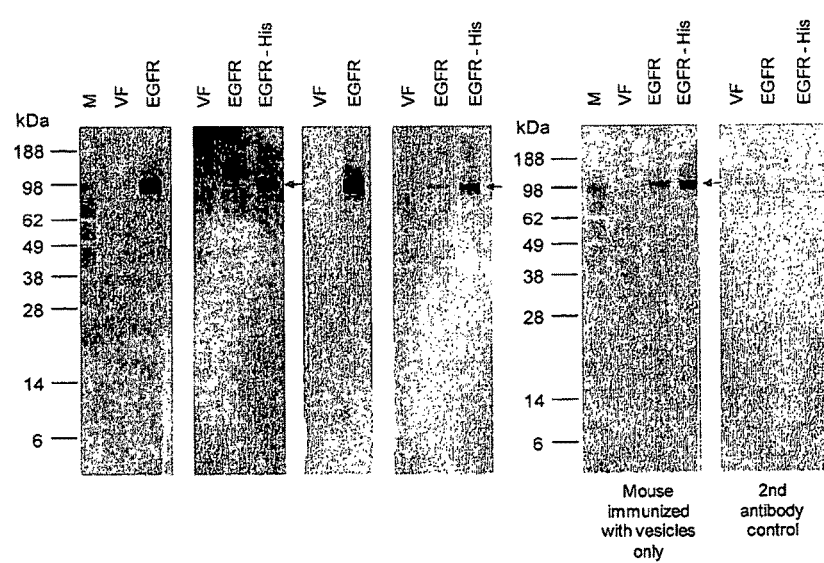

The corresponding results are presented in FIG. 5 and Table 2.

FIG. 5: Western blot analysis of mouse polyclonal antisera gained before and after immunization of mice with insect vesicles containing de novo synthesized Mel-trunc-EGFR. Insect vesicles without Mel-trunc-EGFR and insect vesicles with exogenous cell-free synthesized Mel-trunc-EGFR ("EGFR") were precipitated in acetone and embedded proteins—endogenous proteins as well as the exogenous target protein—were separated in a SDS-PAGE. In addition, cell-free synthesized and purified Mel-trunc-EGFR-His ("EGFR-His") was applied for SDS-PAGE. After successful transfer of proteins on PVDF membranes by semi dry western blot, membrane slices were incubated with polyclonal mouse antisera, followed by incubation with HRP-coupled anti-mouse antibody (anti-mouse conjugated IgG, 1:1000 in blocking buffer). Arrows are indicating detection of Mel-trunc-EGFR/Mel-trunc-EGFR-His. M=protein marker (SeeBlue® Plus2, Life technologies).

TABLE 2

Overview on the performance of polyclonal mouse antiserum analyzed by western blot. Different antigens (untreated insect vesicles, insect vesicles with contained Mel-trunc-EGFR and purified Mel-trunc-EGFR-His) were separated by SDS-PAGE and blotted on PVDF membranes (semi-dry blotting technique). Mouse antisera that were gained after immunization with insect vesicles alone or insect vesicles with embedded Mel-trunc-EGFR were used for detection of Mel-trunc-EGFR and Mel-trunc-EGFR-His, respectively.

| Serum Antigen | Before immunization | After immunization with insect vesicles | After immunization with insect vesicles harboring Mel-trunc-EGFR |
|---|---|---|---|
| Untreated insect vesicles | − | + | + |
| Insect vesicles harboring Mel-trunc-EGFR | − | + | + |

TABLE 2-continued

Overview on the performance of polyclonal mouse antiserum analyzed by western blot. Different antigens (untreated insect vesicles, insect vesicles with contained Mel-trunc-EGFR and purified Mel-trunc-EGFR-His) were separated by SDS-PAGE and blotted on PVDF membranes (semi-dry blotting technique). Mouse antisera that were gained after immunization with insect vesicles alone or insect vesicles with embedded Mel-trunc-EGFR were used for detection of Mel-trunc-EGFR and Mel-trunc-EGFR-His, respectively.

| Serum Antigen | Before immunization | After immunization with insect vesicles | After immunization with insect vesicles harboring Mel-trunc-EGFR |
|---|---|---|---|
| Purified Mel-trunc-EGFR-His | − | − | + |

Minus (−) = No reactivity.
Plus (+) = Detection of proteins.

As expected, appliance of mouse serum gained before immunization did not result in the detection of protein bands. In contrast, mouse antiserum gained after immunization with insect vesicles resulted in detection of many differently sized proteins in lanes with blotted insect vesicles without contained Mel-trunc-EGFR and with Mel-trunc-EGFR. This observation is according to the expectations as insect vesicles contain many different endogenous membrane proteins which are potentially capable of inducing an immune reaction in laboratory animals. Use of mouse serum gained after immunization with insect vesicles and contained Mel-trunc-EGFR resulted in a similar detection pattern. As expected, purified Mel-trunc-EGFR was detected solely by using mouse serum gained after immunization with insect vesicles and contained Mel-trunc-EGFR, but not with mouse antiserum gained after immunization with insect vesicles alone. This observation supports the assumption of a specific detection of Mel-trunc-EGFR by the use of polyclonal mouse serum (immunization with insect vesicles containing cell-free synthesized Mel-trunc-EGFR).

In addition to the use of polyclonal mouse antiserum, a commercially available anti-EGFR antibody was used to demonstrate the successful blotting of Mel-trunc-EGFR in order to validate the obtained results.

For that purpose, primary and secondary antibodies were removed from PVDF membranes by treatment under harsh buffer conditions ("membrane stripping"). After stripping membranes were subsequently incubated with a commercially available anti-EGFR antibody as primary antibody (Anti-EGF receptor D38B1 XP, rabbit monoclonal antibody, 1:1000 in blocking buffer) and HRP-coupled antibody as secondary antibody (HRP-conjugated Anti-rabbit IgG, 1:2000 in blocking buffer). Mel-trunc-EGFR and Mel-trunc-EGFR-His were detected as distinct protein bands demonstrating the presence of the cell-free synthesized protein in the analyzed membrane stripes.

The invention claimed is:

1. A method for producing polyclonal antibodies against an antigenic target protein which comprises inducing an immune response in a host by applying an immunogenic composition comprising membrane vesicles incorporating said antigenic target protein to said host and obtaining antibodies against said target protein from a serum of the host, wherein the membrane vesicles are ER-derived and the antigenic target protein is de novo synthesized in a eukaryotic cell-free system.

2. The method according to claim 1 comprising at least the following steps:
   a) synthesizing the target protein by an in vitro translation reaction in a reaction medium comprising a nucleic acid template coding for the target protein and a cell lysate which contains membrane vesicles;
   b) separating membrane vesicles comprising the target protein from the medium;
   c) providing the membrane vesicles comprising the target protein in a physiologically compatible medium;
   d) applying the membrane vesicles of step c) to a host;
   e) testing a serum sample of the host for a specific immune response against said target protein; and
   f) obtaining specific antibodies against said target protein from the serum of a host exhibiting a specific immune response against said target protein.

3. The method according to claim 2 wherein the cell lysate is a eukaryotic cell lysate.

4. The method according to claim 3 wherein the cell lysate is a member selected from the group consisting of wheat germ lysates, insect cell lysates, reticulocyte lysates, keratinocyte lysates, cell extracts from CHO cells, HeLa cells, myeloma cells, hybridoma cells and cultivated lymphoma cells.

5. The method according to claim 2, wherein the membrane vesicles and the cell lysate are derived from the same cell line.

6. The method according to claim 2, wherein the membrane vesicles comprising the target protein are separated from the medium by centrifugation.

7. The method according to claim 2, wherein the in vitro translation reaction in step a) is effected under conditions which promote enrichment of the target protein in the membrane vesicles.

8. The method according to claim 7, wherein step b) is followed by an additional step b') which comprises transferring the separated membrane vesicles into a secondary reaction medium comprising a nucleic acid template coding for the target protein and a cell lysate which does not contain membrane vesicles, performing an in vitro translation reaction in said secondary reaction medium, and separating membrane vesicles comprising an increased amount of the synthesized target protein from the secondary medium, wherein step b' may be repeated one or more times.

9. The method according to claim 7, wherein the in vitro translation reaction in step a) is performed by a continuous dialysis-based method involving the addition and/or discharge of reactants or products in a course of the translation reaction.

10. The method according to claim 9, wherein the in vitro translation reaction in step a) is performed in a presence of a caspase inhibitor.

11. The method according to claim 1, wherein the immunogenic composition does not contain any immunostimulatory adjuvant additional to the membrane vesicles incorporating the antigenic target protein.

12. The method according to claim 1, wherein the host is a non-human mammal.

13. A method for accumulating a target protein in vesicles of a membrane vesicle preparation, comprising at least the following steps:
   a) synthesizing the target protein by an in vitro translation reaction in a reaction medium comprising a nucleic acid template coding for the target protein and a cell lysate which contains membrane vesicles;

b) separating membrane vesicles comprising the target protein from the medium to provide separated membrane vesicles;
c) transferring the separated membrane vesicles into a secondary reaction medium comprising a nucleic acid template coding for the target protein and a cell lysate which does not contain membrane vesicles, performing an in vitro translation reaction in said secondary reaction medium, and separating membrane vesicles comprising an increased amount of the target protein from the secondary medium, wherein step c) may be repeated one or more times.

14. The method of claim 4, wherein the cell lysate is an Sf21 cell lysate.

* * * * *